(12) United States Patent
Nehlen, III

(10) Patent No.: US 9,581,395 B2
(45) Date of Patent: *Feb. 28, 2017

(54) MULTI-SEGMENTED TUBE SHEET

(71) Applicant: Neptune-Benson, LLC, Coventry, RI (US)

(72) Inventor: Paul F. Nehlen, III, Delavan, WI (US)

(73) Assignee: Neptune-Benson, LLC, Coventry, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/088,453

(22) Filed: Apr. 1, 2016

(65) Prior Publication Data

US 2016/0216049 A1  Jul. 28, 2016

Related U.S. Application Data

(63) Continuation-in-part of application No. 14/830,994, filed on Aug. 20, 2015, now Pat. No. 9,303,924, (Continued)

(51) Int. Cl.
 *B01D 1/00* (2006.01)
 *B01D 29/50* (2006.01)
 (Continued)

(52) U.S. Cl.
 CPC ............... *F28F 3/12* (2013.01); *A61F 7/00* (2013.01); *B01D 1/00* (2013.01); *B01D 1/0082* (2013.01);
 (Continued)

(58) Field of Classification Search
 CPC ........ B01D 17/12; B01D 25/04; B01D 1/221;
 B01D 1/30; B01D 3/00; B01D 5/0015;
 B01D 35/14; B01D 35/18; B01D 39/10;
 B01D 39/12; B01D 63/08; B01D
 2201/54; B01D 29/0004; B01D 29/0018;
 B01D 29/002;
 (Continued)

(56) References Cited

U.S. PATENT DOCUMENTS 1,947,109 A  2/1934 Potter
1,992,504 A  2/1935 Penniman
(Continued)

FOREIGN PATENT DOCUMENTS

EP  0 777 098  4/1997
EP  1 985 956  10/2008

*Primary Examiner* — Joseph Drodge

(57) ABSTRACT

A heat exchanger that is constructed with a heat exchanger shell having inlet and outlet plenums and fluid inlet and outlet ports, and a tube sheet construction disposed in the heat exchanger shell. The tube sheet construction includes at least two separate tube sheets and a plurality of tubes that extend between the separate tube sheets. Each tube sheet includes at least two planar tube sheet segments and a interstitial layer disposed between the at least two tube sheet segments, and at least one sensor element supported by each of the interstitial layers. A control monitor controls flow through the shell by a feedback control from the sensor to an inlet control valve and/or a stimulus device excites the media layer. In an alternate embodiment opposed position sensor elements may be provided at opposite sides of the tube sheet construction.

22 Claims, 12 Drawing Sheets

Related U.S. Application Data which is a continuation-in-part of application No. 14/535,655, filed on Nov. 7, 2014, now Pat. No. 9,127,896.

(60) Provisional application No. 62/063,681, filed on Oct. 14, 2014.

(51) Int. Cl.

| | | |
|---|---|---|
| *B01D 29/56* | (2006.01) | |
| *F28D 9/00* | (2006.01) | |
| *F28F 3/12* | (2006.01) | |
| *F28F 21/08* | (2006.01) | |
| *F28F 27/00* | (2006.01) | |
| *A61F 7/00* | (2006.01) | |
| *B01D 5/00* | (2006.01) | |
| *F28F 9/007* | (2006.01) | |
| *F28F 9/02* | (2006.01) | |
| *F28D 7/16* | (2006.01) | |
| *F28F 1/00* | (2006.01) | |
| *H01M 2/00* | (2006.01) | |

(52) U.S. Cl.
CPC ............... *B01D 5/00* (2013.01); *F28D 7/16* (2013.01); *F28D 9/0031* (2013.01); *F28F 1/00* (2013.01); *F28F 9/007* (2013.01); *F28F 9/0229* (2013.01); *F28F 9/0275* (2013.01); *F28F 21/082* (2013.01); *F28F 21/087* (2013.01); *F28F 27/00* (2013.01); *H01M 2/00* (2013.01); *F28F 2200/00* (2013.01); *F28F 2210/10* (2013.01)

(58) Field of Classification Search
CPC .............. B01D 29/0029; B01D 29/005; B01D 29/0052; B01D 29/0072; B01D 29/0095; B01D 29/01; B01D 29/012; B01D 29/05; B01D 29/50; B01D 29/56; A61M 1/0272; A61F 7/00; A61F 7/08; F28F 1/00; F28F 1/003; F28F 1/10; F28F 1/42; F28F 1/422; F28F 9/007; F28F 9/013; F28F 9/0131; F28F 9/0132; F28F 9/0133; F28F 9/0137; F28F 3/12; F28F 3/13; F28F 2200/00; F28F 2200/005; F28F 2210/00; F28F 2210/10; F28F 2225/04; F28F 2700/006; F28F 9/0221; F28F 9/0229; F28F 19/00; F28F 27/00; F28F 27/02; F28F 3/00; F28F 3/08; F28F 3/086; F28F 21/08; F28F 21/082; F28F 21/087; F28D 1/04; F28D 1/053; F28D 1/05308; F28D 1/05316; F28D 7/00; F28D 7/0008; F28D 7/0023; F28D 7/16; F28B 9/00; Y10T 9/49364; Y10T 9/49366; Y10T 9/49368; Y10T 29/49364; Y10T 29/49366; Y10T 29/49368

See application file for complete search history.

(56) References Cited

U.S. PATENT DOCUMENTS

| | | |
|---|---|---|
| 2,164,629 A | 7/1939 | Sibley |
| 2,228,549 A | 1/1941 | Young |
| 2,948,517 A | 8/1960 | Cosner |
| 3,114,415 A | 12/1963 | Wintzer |
| 3,181,606 A | 5/1965 | Belanger |
| 3,195,624 A | 7/1965 | Richards et al. |
| 3,326,279 A | 6/1967 | Eisberg et al. |
| 3,472,042 A | 10/1969 | Shriver et al. |
| 3,715,033 A | 2/1973 | Soriente |
| 3,805,889 A | 4/1974 | Coolidge |
| 3,972,371 A | 8/1976 | Plegat |
| 4,105,066 A | 8/1978 | Buhler |
| 4,182,408 A | 1/1980 | Laber |
| 4,421,160 A | 12/1983 | Stafford et al. |
| 4,485,547 A | 12/1984 | Busse |
| 4,609,462 A | 9/1986 | Flynn |
| 4,635,712 A | 1/1987 | Baker et al. |
| 4,640,192 A | 2/1987 | Nash |
| 4,718,483 A | 1/1988 | Artusi |
| 4,782,571 A | 11/1988 | Krips et al. |
| 4,827,605 A | 5/1989 | Krips et al. |
| 4,871,014 A | 10/1989 | Sulzberger |
| 5,128,038 A | 7/1992 | Slavitschek et al. |
| 5,154,679 A | 10/1992 | Fuller et al. |
| 5,630,470 A * | 5/1997 | Lockwood, Jr. ...... F28F 9/0229 165/178 |
| 6,026,804 A | 2/2000 | Schardt et al. |
| 6,206,086 B1 | 3/2001 | McKey |
| 7,048,042 B2 | 5/2006 | Juschka |
| 7,377,039 B2 | 5/2008 | Al-Anizi et al. |
| 7,712,517 B2 | 5/2010 | Gandolfi et al. |
| 8,177,932 B2 | 5/2012 | Becnel et al. |
| 9,127,896 B1 | 9/2015 | Nehlen, III |
| 9,149,742 B1 | 10/2015 | Nehlen, III |
| 9,302,205 B1 * | 4/2016 | Nehlen, III ............ F28F 9/0229 |
| 9,303,924 B1 * | 4/2016 | Nehlen, III ............ F28F 9/0229 |
| 2004/0238161 A1 | 12/2004 | Al-Anizi et al. |
| 2005/0034847 A1 | 2/2005 | Graham et al. |
| 2007/0144716 A1 | 6/2007 | Doh et al. |
| 2008/0099193 A1 * | 5/2008 | Aksamit ................ G05D 23/08 165/300 |
| 2009/0019689 A1 | 1/2009 | Zobel et al. |
| 2010/0243208 A1 | 9/2010 | Kar et al. |
| 2013/0233508 A1 * | 9/2013 | Cederberg ............. F28F 3/083 165/11.1 |
| 2013/0336359 A1 * | 12/2013 | Zink ...................... G01K 7/023 374/152 |

* cited by examiner

MULTI-SEGMENTED TUBE SHEET

RELATED CASES

This application is a continuation-in-part (CIP) of U.S. Ser. No. 14/830,994 filed on Aug. 20, 2015 which is scheduled to issue as U.S. Pat. No. 9,303,924 on Apr. 5, 2016 which is a continuation-in-part (CIP) of U.S. Ser. No. 14/535,655 filed on Nov. 7, 2014 which is now U.S. Pat. No. 9,127,896 which issued on Sep. 8, 2015 and which claims priority to under 35 U.S.C. §119 (e) to commonly owned and U.S. Provisional Patent Application No. 62/063,681 which was filed on Oct. 14, 2014, and which is incorporated by reference herein in its entirety. Reference is also made to co-pending application Ser. No. 14/535,596 filed on Nov. 7, 2014 now U.S. Pat. No. 9,149,742 which issued on Oct. 6, 2015, and a co-pending continuation-in-part (CIP) application U.S. Ser. No. 14/830,956 filed on Aug. 20, 2015 and which is set to issue as U.S. Pat. No. 9,302,205 on Apr. 5, 2016. All of the above identified applications are incorporated by reference herein in their entirety.

FIELD OF THE INVENTION

The present invention relates in general to tube sheets that are typically used in such applications as filtration and heat exchange. More particularly, the present invention relates to an improvement in the construction of a tube sheet that enhances the function of the tube sheet and enables the tube sheet to be manufactured with less expense. Even more particularly the present invention relates to an improved tube sheet construction for providing greater process control by employing an active media layer for a tube sheet used in particular in a heat exchanger construction.

BACKGROUND OF THE INVENTION

In the field of filtration and heat exchange, there is a device commonly used to develop separate regions; commonly referred to as a tube sheet. The tube sheet is meant to be supported in a housing or tank and is used primarily for the support of a plurality of filter or coupling elements that are usually in the form of filter tubes for filtration or heat exchange. By way of example refer to U.S. Pat. Nos. 3,715,033; 4,609,462 and 5,128,038 which describe various filter constructions in which the filter tubes are supported by the tube sheet essentially forming a boundary region by which filtration or even heat exchange can be affected. For heat exchanger application one may refer to U.S. Pat. Nos. 4,485,547; 4,782,571 and 4,827,605 that show the use of tube sheet constructions. The tube sheet provides a support for the tubes, but also functions as a bulkhead to the media on either side of the tube sheet; effectively maintaining a discontinuity so that transformation can take place.

In actual operation, there are times when differential pressures on opposing sides of the tube sheet are in excess of normal operating differential pressures; substantial pressures in and of themselves. In order to overcome the differential pressure and maintain structural rigidity the tube sheet is typically produced of a substantial thickness, and machined to a high tolerance to accept the tubes. One particular disclosure of a tube sheet is shown in the '462 patent as tube sheet 32.

This tube sheet thickness solves the problem of structural rigidity while simultaneously serving the purpose of a bulkhead and a means to maintain the spacing between the tubes. This comes at a cost. The machining process which typically is by drilling or water jet cutting is a slow and costly process to produce the sufficiently rigid, high tolerance barrier required.

In a typical tube sheet construction the tube sheet may be formed of a metal material such as stainless steel and can have a thickness on the order of ½ inch. A sheet of stainless steel is fabricated to various diameters; between less than one foot in diameter up to a diameter of greater than 5 feet in diameter, and then holes [one to 2500 or more holes] are drilled with a conventional drill bit or water jet cutter to facilitate insertion of the tube elements. This process is cumbersome and very time consuming; as much as 20 hours or more to produce one sheet 5 feet in diameter.

The vast majority of tube sheets in use are fabricated in this fashion, whether it is for use in a heat exchanger, filter, for reverse osmosis, distillation, or as a condenser, evaporator, or for fuel cell applications. An objective of the present invention is to provide a multi-segment tube sheet wherein, instead of drilling a one-piece thick plate, the tube sheet is formed in multiple segments which are then fastened together to provide structural rigidity.

Another objective of the present invention is to provide an improved tube sheet which eliminates the costly and time consuming steps to manufacture as with present day tube sheets.

Still another objective of the present invention is to provide an improved tube sheet structure including a stacked assembly of thinner sheets, that when assembled together provide the structural integrity of the present day tube sheet but at a substantially reduced manufacturing cost.

A further objective of the present invention is to provide an improved tube sheet structure including a stacked assembly of thinner sheets, and in which the thinner sheets are more readily processed for creating holes therein such as by being punched on an automated press, burned with a laser or a plasma cutter, or formed by being printed using additive manufacturing technologies; ie 3D printing as but one example.

Another objective of the present invention is to provide an improved tube sheet construction including an interstitial layer referred to herein as a media layer so that the tube sheet functions both as a tube sheet as well as a multifunctional sensor device.

A further objective of the present invention is to provide an improved tube sheet construction that provides, in addition to multiple sheet segments, a unique intermediate layer referred to herein as a media layer for providing any one of a number of additional functions including filtration and the sensing of parameters such as temperature or pressure associated a heat exchange process.

SUMMARY OF THE INVENTION

To accomplish the foregoing and other objects, features and advantages of the present invention there is provided an improved tube sheet structure and associated method of manufacturing such a tube sheet, while solving the above mentioned problems associated with present tube sheet constructions. The present invention solves the problem of maintaining the high tolerance, tube spacing, and structural rigidity of the tube sheet. This is achieved in accordance with the present invention by manufacturing the tube sheet out of multiple thinner layers of sheet that are critically aligned to each other and to the tubes in the assembly process, and then fixing this assembly together to achieve the final structural integrity and bulkhead characteristics of a tube sheet.

For the present invention the same end-use tube sheet in this arrangement will take a fraction of the time to manufacture, due primarily to the substantially reduced thickness of individual sheets, if punched on an automated press, burned with a laser or a plasma cutter, or printed using additive manufacturing technologies [ie 3D printing as but one example] and assembled and fixed. An added feature in accordance with the present invention is that layering of the tube sheet allows interstitial placement of materials creating a non-homogeneous device that in its entirety functions both as a tube sheet as well as a multifunctional filtration device or membrane. Fixing the thin sheets into contact serves the purpose of maintaining the bulkhead effect and the structural integrity, as well as the desired tube spacing. One or more fasteners are used to secure all layers or sheets together as a unitary mass functioning as a tube sheet. By "fasteners" reference can be made to any one of a number of devices or techniques by which the individual layers or sheets are secured together.

To accomplish the foregoing and other objects, features and advantages of the present invention there is provided a tube sheet construction that includes at least two planar tube sheet segments, multiple holes being provided in each sheet in a predetermined pattern, each hole for accommodating a tube sheet tube, the tube sheet segments being aligning so that all hole patterns of each sheet align, an interstitial layer disposed between the at least two tube sheet segments, and at least one sensor element supported by the interstitial layer.

In accordance with other aspects of the present invention including fasteners for securing the tube sheet segments and interstitial layer together; including a control monitor external to the tube sheet construction and responsive to a signal from the sensor element; wherein the sensor element senses temperature; including multiple sensor elements all disposed within the interstitial layer; wherein the sensor element senses pressure; including a plurality of tube sheets constructed and arranged for the support of the tube sheet tubes therebetween; including an interstitial layer with each tube sheet and each separate sensor element sensing a pressure at its respective tube sheet; including a plurality of tube sheets constructed and arranged for the support of the tube sheet tubes therebetween; including a control monitor external to the tube sheets and responsive to a signal from the respective sensor elements to determine differential pressure.

In accordance with another embodiment of the present invention there is provided a heat exchanger that is comprised of a heat exchanger shell having inlet and outlet plenums and fluid inlet and outlet ports, and a tube sheet construction disposed in the heat exchanger shell, the tube sheet construction including at least two separate tube sheets and a plurality of tubes that extend between the separate tube sheets, wherein each tube sheet includes at least two planar tube sheet segments and an interstitial layer disposed between the at least two tube sheet segments, and at least one sensor element supported by each of the interstitial layers.

In accordance with still other aspects of the present invention including multiple holes being provided in each tube sheet in a predetermined pattern, each hole for accommodating a tube sheet tube, the tube sheet segments being aligning so that all hole patterns of each sheet align; including fasteners for securing the tube sheet segments and interstitial layer together; including a control monitor external to the tube sheet construction and responsive to a signal from each sensor element; wherein the sensor element senses temperature; including multiple sensor elements all disposed within the interstitial layer; wherein the sensor element senses pressure; including at least three tube sheets constructed and arranged for the support of the tube sheet tubes therebetween.

In another embodiment of the present invention there is provided a combination of a tube sheet and a plurality of elongated tubular elements supported with the tube sheet, said tube sheet comprised of a plurality of separate planar tube sheet segments, and multiple holes being provided in each planar tube sheet segment in a predetermined pattern, each hole for accommodating one of the plurality of elongated tubular elements, all of the tube sheet segments being aligning so that the hole pattern of each segment aligns with the hole pattern in all other segments. Each elongated tubular element has a flanged top end and a contiguous tubular shaft with the flanged top end having a diameter greater than a diameter of the tubular shaft, said flanged top end supported over a first one of said plurality of separate planar tube sheet segments, and a securing piece constructed and arranged about the tubular shaft of the elongated tubular element and supported under a second one of said plurality of separate planar tube sheet segments. The securing piece is for engagement with the tubular shaft to provide a compressive force against the tube sheet segments that are disposed between the flanged top end and the securing piece.

In accordance with another version of the present invention there is provided a tube sheet construction that is comprised of a plurality of separate planar tube sheet segments, multiple holes being provided in each planar tube sheet segment in a predetermined pattern, each hole for accommodating an elongated tubular element, an active planar layer disposed parallel with the plurality of separate tube sheet segments, and fasteners for securing all of the planar tube sheet segments and the active planar layer together and arranged so that all planar tube sheet segments and said active planar layer are maintained in intimate contact. The active layer comprises a layer in which one of an external stimulus is applied to the layer and a response is elicited from the layer.

In still another version of the present invention there is provided a tube sheet construction that is comprised of a plurality of separate planar tube sheet segments, multiple holes being provided in each planar tube sheet segment in a predetermined pattern, each hole for accommodating an elongated tubular element, a passive planar layer disposed parallel with the plurality of separate tube sheet segments, and fasteners for securing all of the planar tube sheet segments and the passive planar layer together and arranged so that all planar tube sheet segments and said passive planar layer are maintained in intimate contact. The passive layer is formed as a flow control layer.

BRIEF DESCRIPTION OF THE DRAWINGS

It should be understood that the drawings are provided for the purpose of illustration only and are not intended to define the limits of the disclosure. In the drawings depicting the present invention, all dimensions are to scale. The foregoing and other objects and advantages of the embodiments described herein will become apparent with reference to the following detailed description when taken in conjunction with the accompanying drawings in which.

PRIOR ART DIAGRAM

Figure 1:
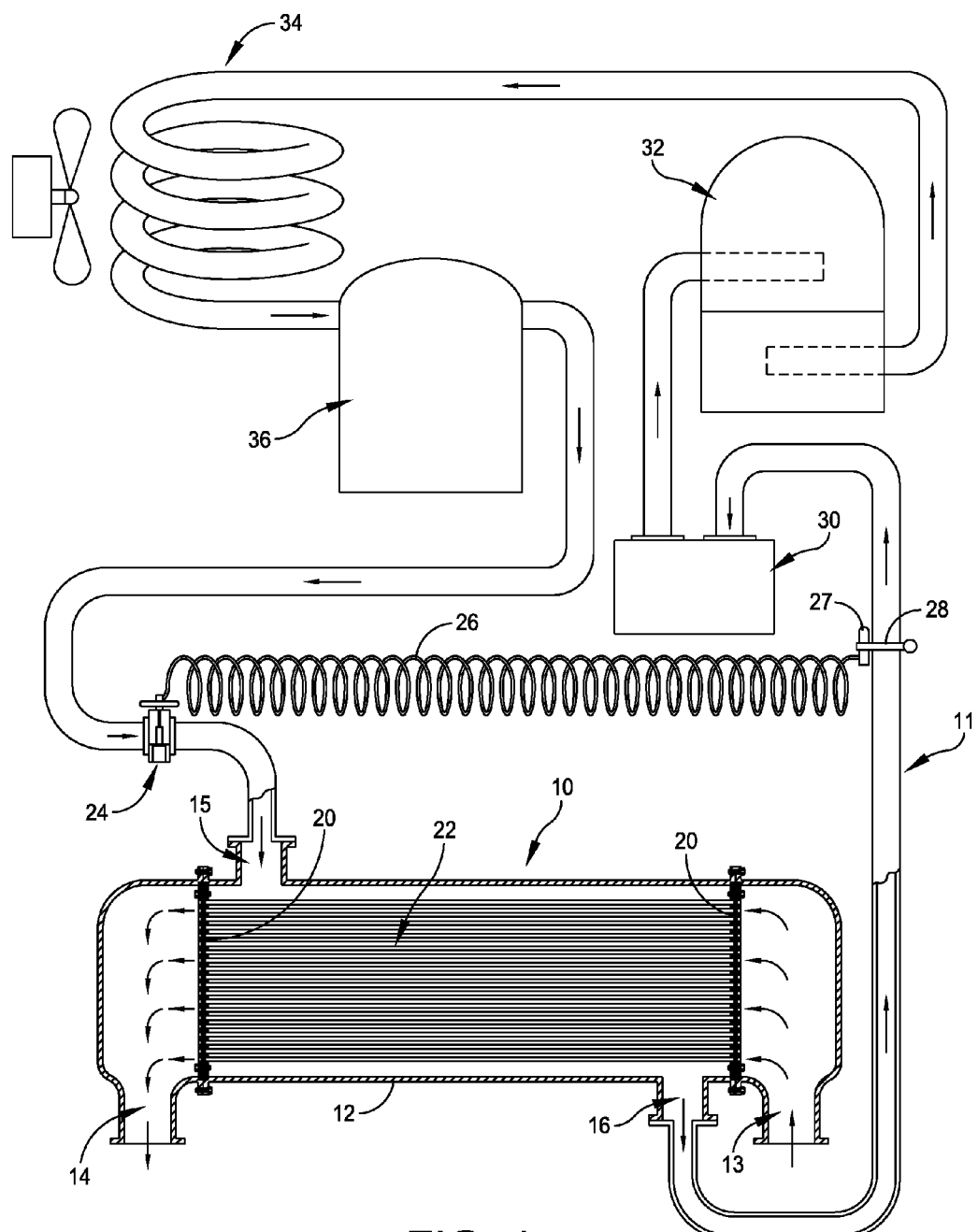
FIG. 1 is a schematic diagram of a prior art heat exchanger system.

Refer now to FIG. 1 there is illustrated a typical control system for the heat exchanger 10. This includes a feedback loop 17 having several lengths of coupling piping for interconnecting components that form the feedback loop 17. This feedback loop essentially extends from the shell side outlet 16 of the shell 12, through the various components shown in FIG. 1 and back to the shell side inlet 15 of the shell 12. The basic heat exchanger construction is formed by the shell 12 and the tube sheet structure that is comprised of a pair of solid tube sheets 20 spacedly supported internally from the shell and a plurality of tubes supported by the tube sheets and extending therebetween. FIG. 1 also depicts the tube side inlet at 13 and the tube side outlet at 14 where the main fluid is being processed. In FIG. 1 the tube sheets 20 are considered as of conventional design; in other words constructed of a one-piece solid metal member.

The aforementioned feedback loop 17 is considered as including, in series, a suction accumulator 30, a hermetic compressor 32, a fan cooled condenser 34 and a receiving tank 36, the function of which is well known in the art. In this arrangement one of the control elements includes a thermal expansion valve 24 that is controlled via the capillary 26 from a detection bulb 27. The TXV thermal expansion valve 24 is of the diaphragm type having a coarse presetting of the valve seat relative to the valve stem of the valve 24. In such an arrangement the diaphragm mounted valve stem of the valve controls the flow through the valve stem/seat pair. This control of the valve 24 is from the pressure bulb 27 by way of the gas filled capillary tube 26 spanning the distance from the TXV bulb 27 to the diaphragm of the thermal expansion valve 24. Under operating conditions, the controlled flow of the shell side of the heat exchanger provides feedback to the TXV thermal expansion valve 24 in order to control fluid flow about the tubes 22 that are mounted between the respective tube sheets 20.

The feedback control loop controls modulating the gas or liquid entering the shell side of a heat exchanger at 15 and exiting at 16 in FIG. 1 by the action of a gas filled bulb 27 fitted to a capillary tube 26; the other end of which is connected to the diaphragm of the TXV thermal expansion valve 24. This bulb 27 is clamped by clamp 28 so as to be in intimate contact with the piping, along with the preferred use of a thermal paste at the bulb 27.

The temperature of the process gas, which is a function of the heat load rejected as the tube side fluid passes, causes a change in gas pressure in the bulb 27 which is transmitted through the capillary tube 26, to the diaphragm of the TXV thermal expansion valve 24. This is a risky endeavor because the precise location of the TXV bulb 27 is not assured, nor is there perfect conduction of the temperature or consideration for the manufacturing tolerances of the multitude of devices that have to work in concert to cause the valve actuation to control the flow at valve 24, which ultimately determines the volume of heat transfer fluid available to change the temperature of the fluid transiting the tube side of the heat exchanger.

DETAILED DESCRIPTION OF ALTERNATE EMBODIMENTS

As mentioned before, in accordance with the present invention the tube sheet is constructed out of multiple thinner layers of sheet material that are aligned to each other and to the tubes in the assembly process, and then fixing this assembly together to achieve the final structural integrity and bulkhead characteristics of a tube sheet. In the drawings of U.S. Pat. No. 9,149,742 which issued on Oct. 6, 2015 which is hereby incorporated by reference herein in its entirety, several different versions of tube sheet constructions are set forth such as in FIGS. 1-4, along with a diagram in FIG. 5 which is an illustration of the application of the principles of the present invention to a filtration structure.

Figure 7:
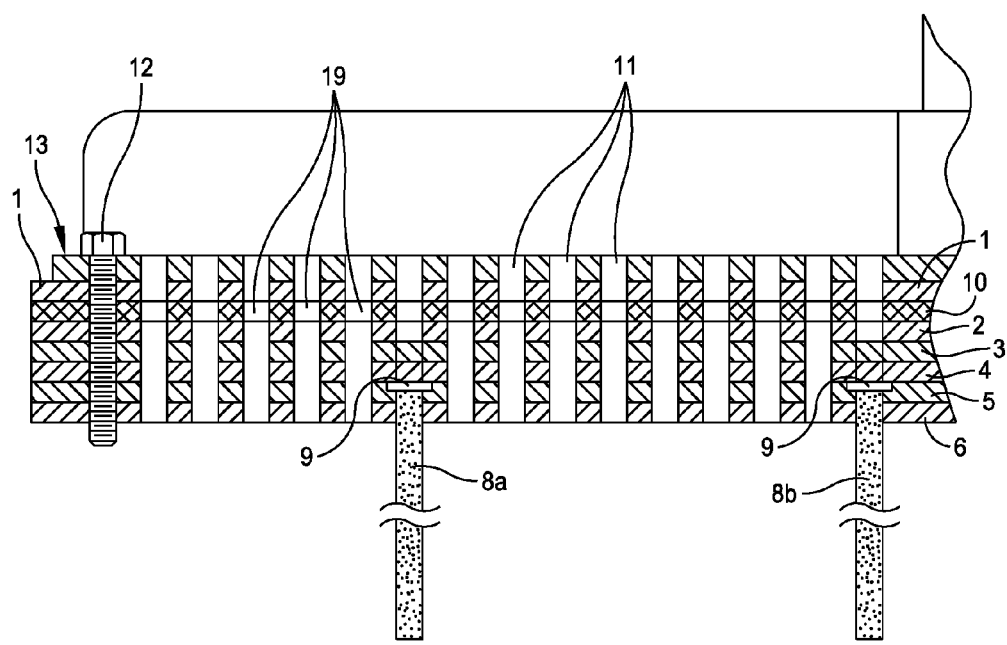
FIG. 7 is a cross-sectional view through an alternate embodiment of a tube sheet.

In accordance with one aspect of the present invention there is provided a method of manufacturing a tube sheet by forming a plurality of separate thin tube sheet segments such as shown in FIG. 7 as layers or sheets 1-6. The next step is forming multiple holes in each sheet in a predetermined pattern such as illustrated at 11. Each hole 11 is for accommodating a tube sheet filter tube 8. A next step is aligning all of the plurality of tube sheet segments 1-6 so that the hole pattern of each sheet aligns with the hole pattern in all other sheets of the plurality of tube sheet segments and securing all of the tube sheet segments together to form a unitary tube sheet such as with the use of fasteners 12 in the embodiment of FIG. 7. Most likely several fasteners would be employed throughout the tube sheet in order to provide a secured unitary structure. All fasteners or other securing means is meant to hold all sheets or layers together. In this embodiment, as well as in other embodiments described herein, the fasteners are arranged so that all separate layers are held in intimate contact with an adjacent layer so as to maintain a solid tube sheet structure without any gaps between layers. This intimate contact also applies to contact with any media layer that is used.

Additionally, one aspect of the present invention allows for stacking, not just the tube sheet layers, but in effect the stacking and retention of other filtration or conversion media between the segmented tube sheet layers. One can envision a circumstance where, in this now discontinuous tube sheet device, the interstitial layer is attached to electrical contacts and the interstitial layer is itself a device that counts passing target molecules (see the sensing circuit 87 in FIG. 6 as an example of a means by which counting can occur). This extra media sheet is illustrated in the drawings herein. For instance, the media layer may be in the form of an energized interstitial layer that is able to sense any number of differences across the breadth of the device such as, for example, differential pressure where a single heat exchanger utilizes a plurality of tube sheets. Yet another envisioned interstitial layer within one or more layers of the tube sheet could be used for measuring the temperature differential across the tube sheet and providing feeding back in real time to enhance computational fluid dynamics software to form an improved open or closed-loop arrangement that enables a new type of highly interactive tube sheet construction.

It is noted that the "media" layer, identified herein by a layer 10 in the drawings and also referred to as an interstitial layer, can take on a multitude of forms. Such a media layer is, for on thing, of a different material than that of the other layers comprising the tube sheet. This layer may be referred to herein in this particular application as being either a "passive layer" or an "active layer. In either case this layer describes an intermediate layer that is essentially a subcomponent of the whole assembly (tube sheet) but working in concert with the whole assembly to provide unique characteristics not possible with existing tube sheet constructions. A "passive" layer may be considered as one in which, by the selection of different materials for that layer (and different than other layers of the tube sheet), one can provide different effects upon the fluid flow through the system, while at the same time not being considered as providing any active stimulus or response. An "active" layer, on the other hand, may be considered as one in which either an external stimulus is applied to the layer or a response is elicited from the layer. Examples of a "passive" layer are where the media layer provides filtration, flow control, shock absorption, magnetic characteristics, dosing, chemical or medical treatment, or ion exchange. Examples of an "active" layer are where the media layer is used to sense a parameter within the tube sheet such as pressure or temperature (response) or where the media layer is externally excited such as by applying a magnetic field to the layer (stimulus). Other examples are set forth herein.

For filtration and heat exchange applications it is common to construct the tube sheet of a metal material such as stainless steel. However, in accordance with the present invention the tube sheet, or certain layers thereof, can also be formed of an insulative or non-metal material such as a glass reinforced plastic material. Also, alternating conductive and non-conductive materials for the various layers can be provided, examples of which are set forth later.

Figure 2:
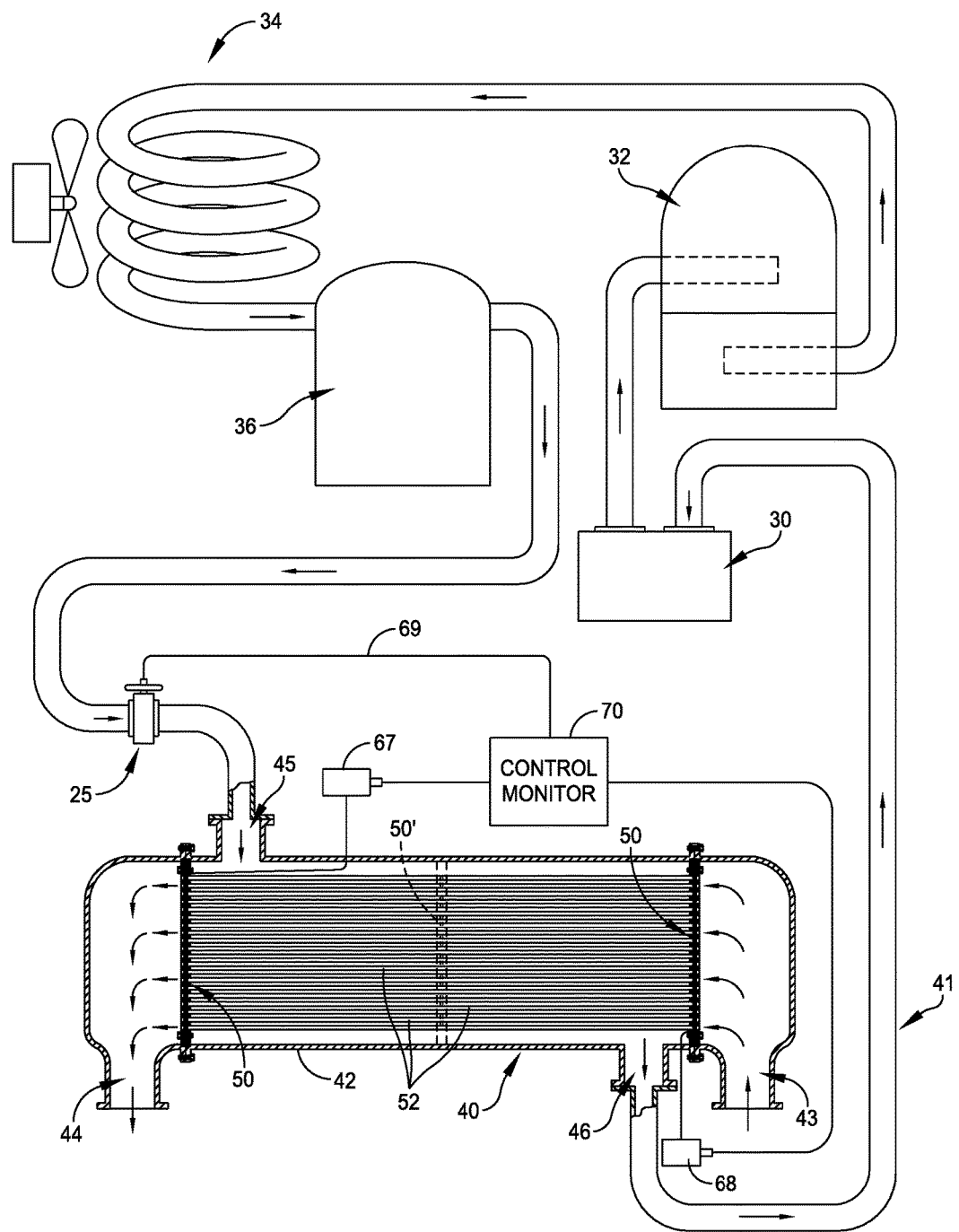
FIG. 2 is a schematic diagram of a heat exchanger system incorporating the improved heat exchanger construction particularly an improved tube sheet construction associated with the heat exchanger.

Referring now to FIGS. 2, 3, 3A and 4, a typical tube sheet heat exchanger apparatus is shown at 40 and of the type to which the present invention is directed to improve upon system operation by the incorporation of the improved tube sheet construction of the present invention. As opposed to, for example, an indirect measurement of the temperature somewhere on the exiting shell side tube, direct measurements of the temperatures can now be taken within the tube sheet itself. This is accomplished by means of incorporating within a separate media layer of the tube sheet sensors, which for this particular embodiment are temperature sensors, such as sensors 65 depicted in FIGS. 3A and 4. In another embodiment described herein pressure is sensed, and in still other embodiments any number of other parameters can be sensed directly within the tube sheet itself. With sensors n=1 to no upper limit, embedded in the media layer 60 of FIG. 3A, a remarkable temperature resolution may be discerned directly and acted upon appropriately with one of several new opportunistically devised control algorithms designed with the new embodiment of the tube sheet device in mind. For instance, one can decouple the bulb and capillary arrangement (see FIG. 1) and, for example, fit a control valve with a stepper motor; in other words an EXV electronic expansion valve 25 (see FIG. 2); driven by the control monitor 70 that may run an algorithm that is capturing real time data at potentially every entrance and every exit of the tubes in the tube sheet, as well as at intermediate positions of the heat exchanger tubes. In FIG. 2 the improvement in accordance with the present invention is set forth while still illustrating the known components of the suction accumulator 30, hermetic condenser 32, fan cooled compressor 34 and receiving tank 36.

Figures 3, 3A:
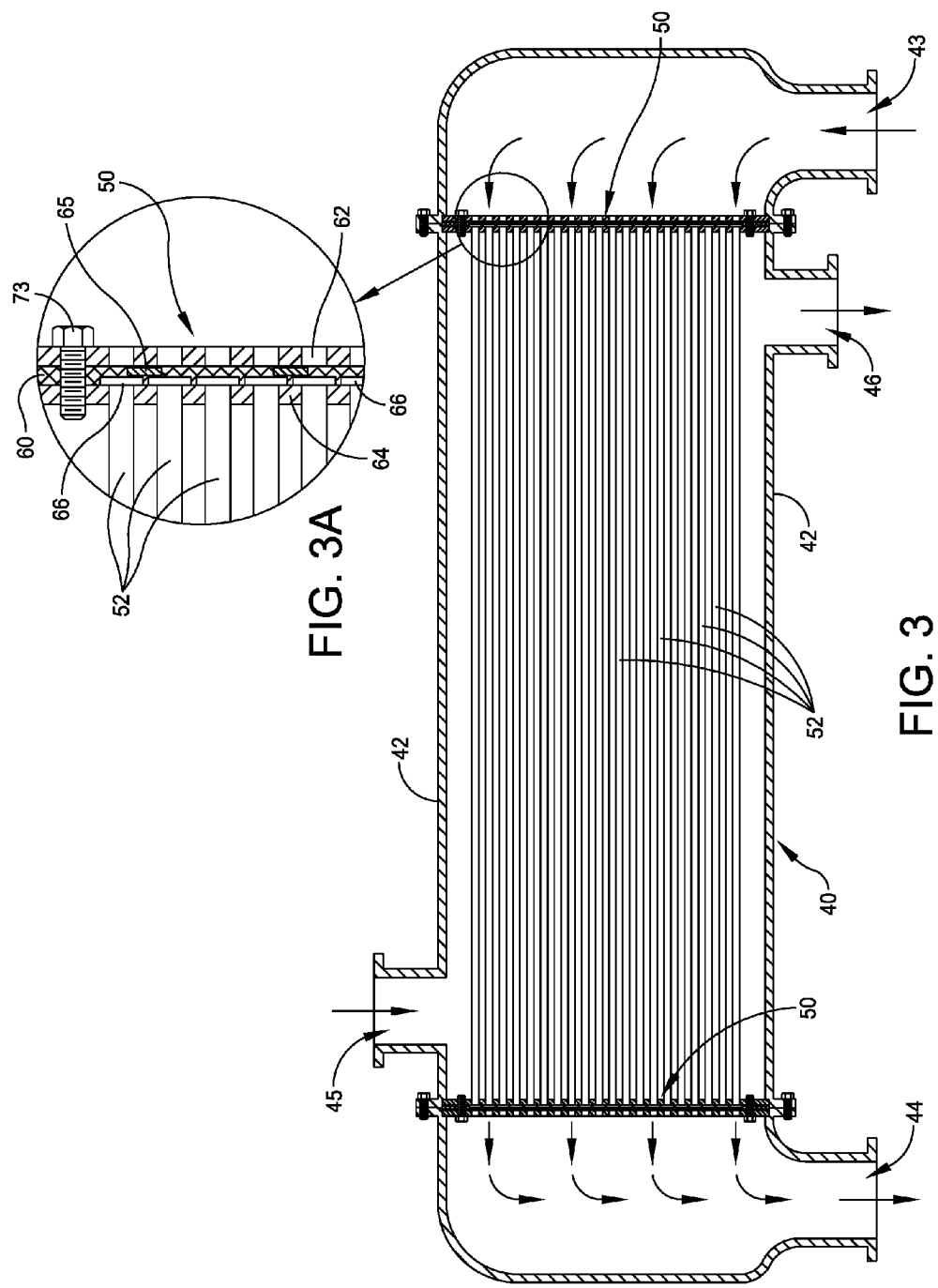
FIG. 3 is an enlarged view of the heat exchanger vessel incorporating an improved tube sheet construction.
FIG. 3A is an enlarged but fragmentary cross-sectional of one of the tube sheets shown in FIG. 3.

In FIGS. 2 and 3 the placement of the tube sheets 50 is illustrated. In this particular embodiment the tube sheets 50 are illustrated as installed at both ends of the heat exchanger in FIG. 3 resulting in improved operating characteristics and energy efficiency of the heat exchanger. This provides for the refinement of computational fluid dynamics (CFD) software and the modeling and construction of more efficient heat exchangers. The control of the heat exchanger will also become more standardized because, unlike with the capillary tube and bulb arrangement, the sensors 65 embedded in layer 60 will remain in intimate contact with the layer and in the precise location with respect to the process measurements necessary to optimize the system. Additionally, if one temperature sensor fails, the system will continue to operate at a very high level of reliability. If one item fails in the temperature feedback loop in the prior art system in a heat exchanger example, control is lost and the system fails. The present invention utilizes increased operational efficiency, and reliability of a heat exchanger. FIG. 2 also illustrates in dotted outline an optional further tube sheet 50' spaced between the end tube sheets. The tubes 52 may pass through this center tube sheet 50' or may be connected in various ways at the center tube sheet 50'. Also, additional tube sheets with a sensor layer may be employed along the tubes in order to facilitate additional measurements; including, but not limited to, such measurements as temperature, force or pressure.

Figure 4:
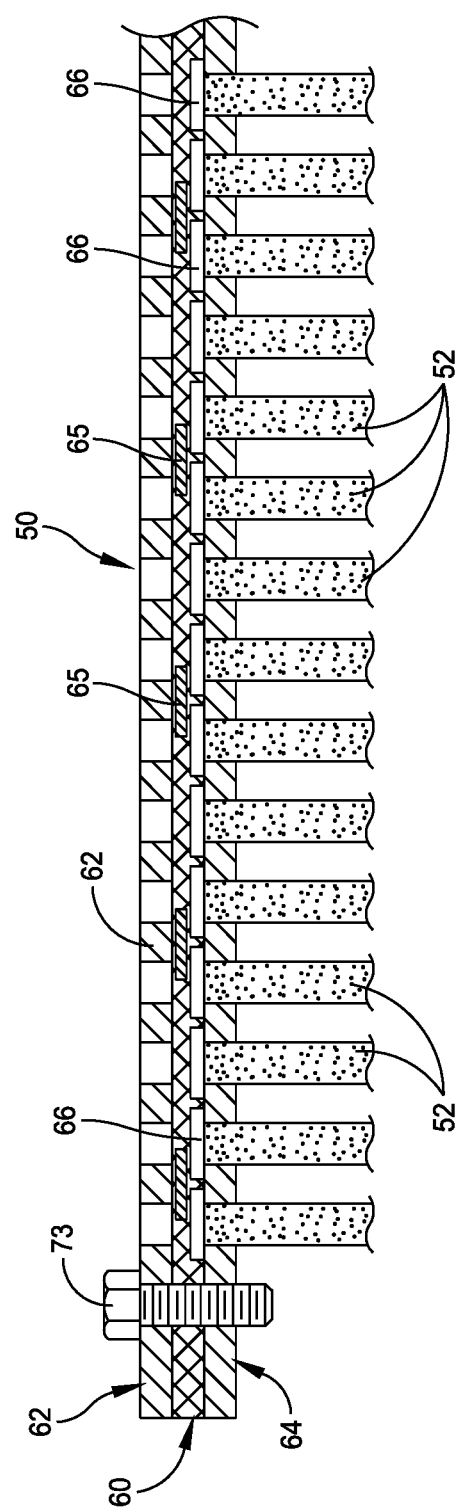
FIG. 4 is an enlarged cross-sectional view through the tube sheet construction.

FIGS. 3, 3A and 4 illustrate further details of the improved tube sheet construction including a multi-segmented tube sheet 60, where n=2 is the minimum number of separate sheets and there is no upper limit; and the minimum tube count n=1 and there is no upper limit. In this particular embodiment the multi-segmented tube sheet is shown with only two main sheets identified as sheets 62 and 64 arranged such that the tubes 52 have ends thereof basically supported between the sheets or segments 62 and 64. In addition there is shown the single media sheet or layer 60 disposed just below the top sheet 62 as viewed in FIG. 4. In this particular embodiment there is provided a flanged surface 66 of each tube 52 and that is disposed essentially between the two sheets 62 and 64. The flange 66 is considered as a part of and affixed at the end of each tube 52 and is the means by which the tubes are held in place relative to the sheets. The first sheet 62 essentially functions in this case as a hold down to the tubular elements 52 and all other sheets including the additional sensing layer 60 that may act as a filtration barrier or a conversion medium to the process media as it passes from the unprocessed side to the processed side, and which may or may not be installed at this location depending on the desired action on the media as it transitions from the primary to the secondary side of the tube sheet. The tube sheet stack in the assembled form may be permanently constructed as with rivets, weld, solder, braze, epoxy, etc. (see fasteners 73) or constructed with removable fasteners such as bolts, screws, removable rivets, etc. or simply floated between some reference points to facilitate loading of the media while simultaneously serving the purpose of a traditional tube sheet acting simply as a bulkhead and the demarcation location between the primary and secondary sides of the tube sheet.

In the embodiment shown in FIGS. 2-4 there are multiple sensors 65 imbedded in the sensing layer 60. However, even a single sensor can be provided per sensing layer. Also, more than two segments of tube sheet media layers can be provided in which case temperature sensing can occur at multiple locations of the tube sheet. In this regard refer to U.S. Pat. No. 9,302,205 which issued on Oct. 6, 2015 and which is hereby incorporated by reference herein in its entirety, and which illustrates several different tube sheet constructions having multiple layers such as six layers shown in one embodiment. In one embodiment there are several separated media layers in a single tube sheet construction. In that case one or more sensors could be imbedded in one or more of these sensing layers. Also, more than two tube sheets may be employed with each spaced along a transverse length of the heat exchanger or filter. The more tube sheets provided, each having a sensing media layer, the broader spectrum one can obtain of the sensed parameter.

Figure 5:
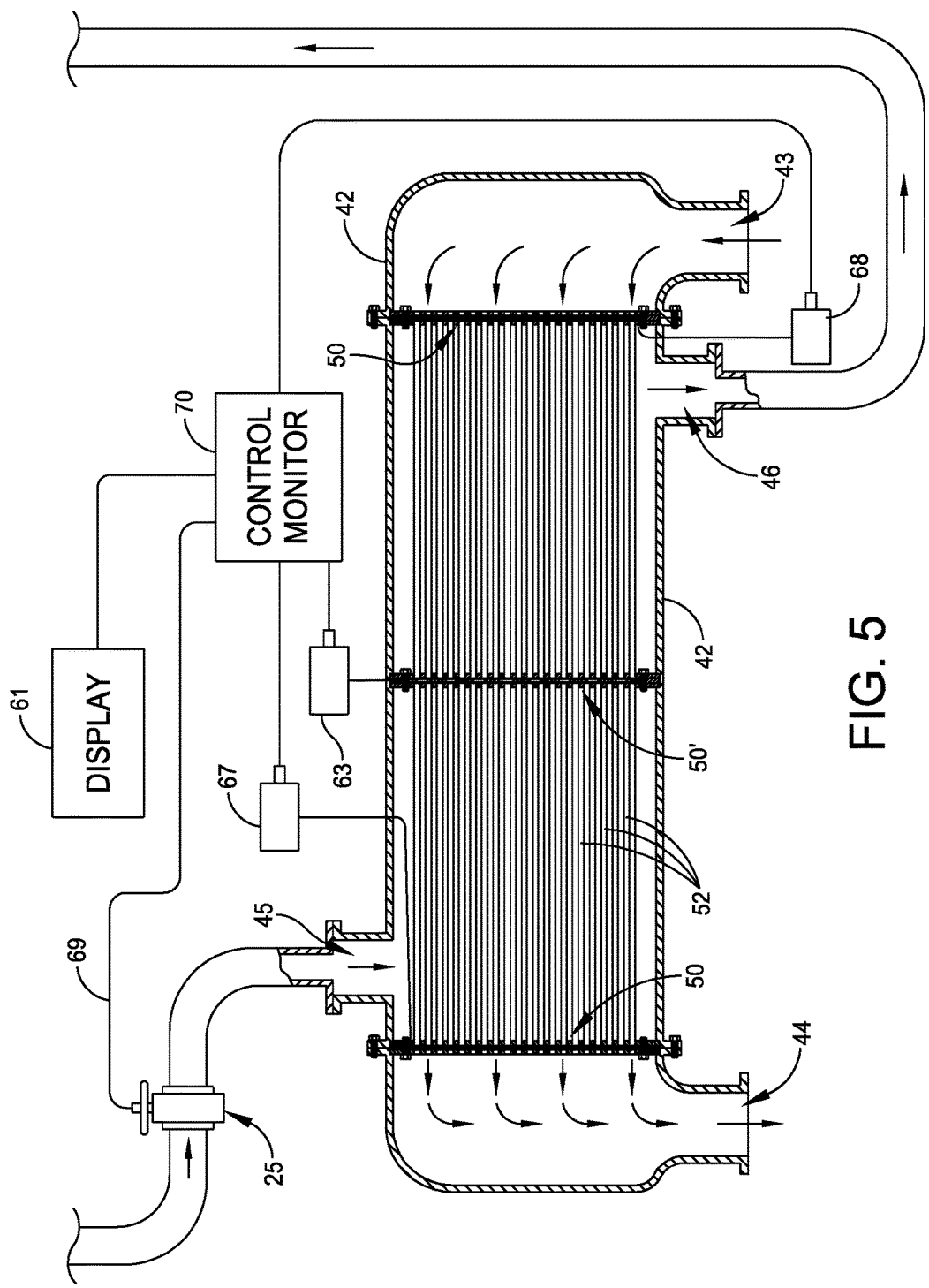
FIG. 5 is a schematic diagram of an alternate embodiment of the present invention showing the use of a control monitor for sensing differential pressures within the tube sheet construction.

In FIG. 2 herein there is depicted in dotted outline a middle tube sheet 50'. Additional tube sheets may also be stacked along the tubes with each having the capability of having one or more sensing layers using one or more temperature or other parameter sensors. In that case the one or more sensors of the middle tube sheet 50' would also connect to the illustrated control monitor 70. Refer also to FIG. 5 discussed hereinafter for an illustration of the use of a middle tube sheet 50' having signals also coupling from that tube sheet to the control monitor 70. The middle tube sheet 50' is permeable to flow from 45 to 46.

In FIG. 2, in addition to the control monitor 70 there is also depicted a receiver box 67 that essentially represents the receipt of a signal from a sensor, or more than one sensor, on or imbedded in the layer 60 of one of the tube sheets 50, and a receiver box 68 that essentially represents the receipt of a signal from a sensor, or more than one sensor, on or imbedded in the layer 60 of the opposed tube sheet 50. Thus, there is illustrated in FIG. 2 control lines that connect each box 67, 68 with a corresponding tube sheet sensor 65, and coupling from there to the control monitor 70. The output of the control monitor at line 69 connects to the valve 25 to control flow through the valve 25 under electronic control from the control monitor 70.

In FIG. 5 there is illustrated another embodiment of the present invention in which differential pressures are measured. In FIG. 5 many of the same reference numbers are used as previously described in FIG. 2. In addition to the output of the control monitor 70 coupling to the valve 25, it is also noted that the differential pressure can be displayed at the display 61. In FIG. 5, in addition to the control monitor 70 there is also depicted a receiver box 67 that essentially represents the receipt of a signal from a sensor, or more than one sensor, on or imbedded in the layer 60 of one of the tube sheets 50, and a receiver box 68 that essentially represents the receipt of a signal from a sensor, or more than one sensor, on or imbedded in the layer 60 of the opposed tube sheet 50, and a third receiver box 63 that essentially represents the receipt of a signal from a sensor, or more than one sensor, on or imbedded in the layer 60 of the middle tube sheet 50'. Thus, there is illustrated in FIG. 2 control lines that connect each box 63, 67, 68 with a corresponding tube sheet sensor or sensors, and coupling from there to the control monitor 70. The output of the control monitor 70 at line 69 connects to the valve 25 to control flow through the valve 25 under electronic control from the control monitor 70.

The following are additional examples of various embodiments of the present invention using primarily active media layers either using a response or stimulus concept. For the "response" concept this means that a sensing occurs from certain sensors at the media layer. For the "stimulus" concept this means that there is an external stimulating of an element at the media layer. An example of a "stimulus" concept is schematically illustrated in FIG. 6 wherein the control monitor is substituted by a stimulus device 80 for imparting a stimulus to the media layer of the tube sheet.

Figure 6:
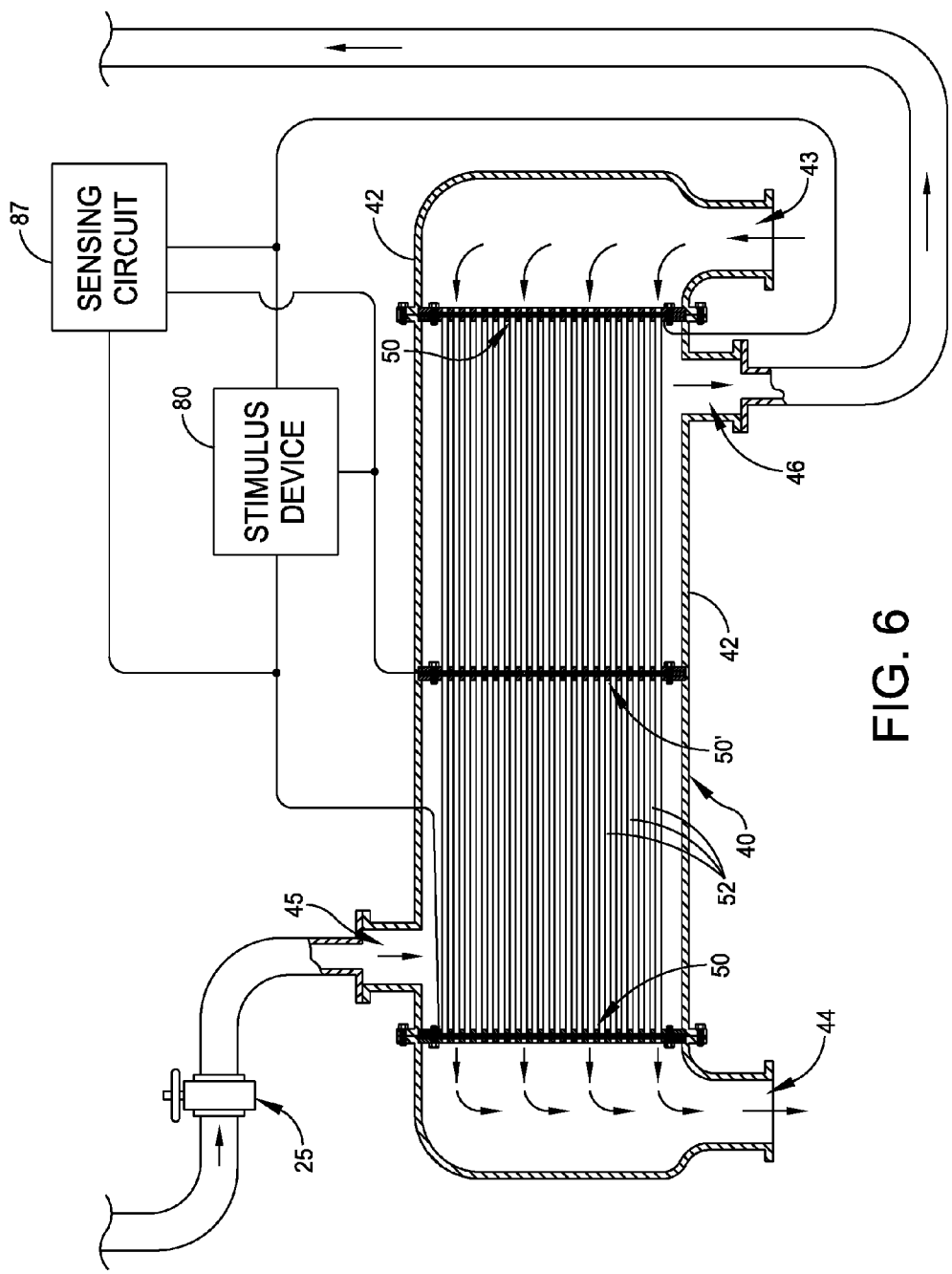
FIG. 6 is a schematic diagram of a still further version of the present invention showing the use of a stimulus device for exciting a media layer, as well as a sensing circuit.

With reference to a tube sheet construction as in FIGS. 3A and 4, and with the excitation concept of FIG. 6, the main layers 62 and 64 may be a pair of respective insulative layers. These layers 62 and 64 may be constructed of non-conductive material such as a glass reinforced plastic and the interstitial layer 60 made of a sintered copper. A charge is then imparted on layer 60 by means of the stimulus device 80 which is schematically illustrated in FIG. 6. This stimulus device connects directly to layer 60 to impart an electrical or magnetic charge or bias on layer 60. The stimulus device 80 may comprise an electrical charging circuit, battery device, or magnetic flux device. This well insulated media layer 60, between insulated layers 62 and 64 functions as an electrostatic filter within the superstructure of the tube sheet device. As flow passes through the tube sheet in FIG. 6, the flow passes through an energized metallic layer 60 placed between layers 62 and 64, particles are trapped on the surface of layer 60. Reversing the flow to back flush layer 60 removes or reverses the charge and releases the particles out of the system.

Another operational arrangement using the tube sheet construction illustrated in FIGS. 3A and 4 provides for magnetic particle filtering. Such filtering can take place in many different applications including for heat exchange, as in U.S. Pat. No. 9,149,742 issued Oct. 6, 2015 as well as in embodiments described herein, and regardless of the number of tube sheet layers that are provided. Thus, the layer 60 in FIG. 4 may be constructed from a material that when activated by an external electric current or coupling with another magnetic field (stimulus device 80 in FIG. 6) be imbued with magnetic properties thus creating the ability to filter out magnetic particulate directly at the tube sheet. In this case, the layers 62 and 64 may be constructed of a non-magnetic material so as not to magnify the strength of the magnetic layer 60, or one may want exactly that effect and in which case the layers 62 and 64 would both be of a material that exhibits magnetic susceptibility, such as those with ferromagnetic (e.g. iron), ferrimagnetic (e.g. magnetite), or antiferromagnetic (e.g. iron manganese, nickel oxide) and in the case of antiferromagnetic organic molecules (e.g. 5-dehydro-m-xylene).

In the example just set forth a further feature can be added so as to essentially provide a hybrid system in which both "stimulus" and "response" is enabled. As indicated above the stimulus device provides an excitation signal to the media layer. In addition an external sensing circuit 87, also depicted in FIG. 6 detects changes in the magnetic flux at layer 60 due to the passing particles of magnetic, ferromagnetic, or antiferromagnetic properties. Now the magnetic layer 60 provides both functions in connection with a sensing device (87) and a filtration device (80), simultaneously or alternatively.

Still another embodiment of the present invention can be practiced in which a plasma layer is essentially established within the tube sheet. Such a plasma layer can be envisioned as being applied to any of the embodiments described herein as well as other embodiments of the tube sheet disclosed in U.S. Pat. No. 9,149,742 issued Oct. 6, 2015. With respect to the tube sheet version illustrated herein in FIG. 4 the layers 62 and 64 are of sufficient construction to contain the plasma therebetween, such as being constructed of a high performance glass material. The gas basis of the plasma is delivered to this interstitial location via some number, where n=1 with no upper limit of modified tubes 52 into the zone between layers 62 and 64. In this case the stimulus is essentially a device for delivering the charge on the gas such that a plasma is created in the zone between layers 62 and 64, or in other words at the layer 60. As flow passes through the tube sheet, it passes through a plasma layer 60 placed between layers 62 and 64. In this way particles are annihilated in an example of this embodiment that may be part of a decontamination heat exchanger.

In still another embodiment for practicing the present invention there is provided an active layer that functions as a UV light delivery zone. In this regard refer to a further version of a tube sheet as illustrated in FIG. 7 herein. In this version layer 4, or other layers, may be a natural or synthetic quartz or engineered glass product that selectively transmits in the UV spectrum. The UV dose is delivered to this interstitial location via some number, where n=1 with no upper limit of fiber-optic tubes 8 into the zone between layers 3 and 5, in other words into layer 4. As flow passes through the tube sheet, it passes through the intersticies of layers 3 to 5. The flow passing will be dosed with UV light emanating from layer 4, and any living matter will have its DNA disrupted or possibly annihilated in an example of this embodiment that may be part of a sanitation device. In FIG. 7 there is provided fiber optic elements or tubes 8a, 8b. The layer 3 reflects into layer 4 but only at the tubes 8a, 8b. At the location of the tubes aligned holes in other layers are optional.

A further embodiment that is contemplated provides the media layer as one that can control the flow level through the tube sheet by means of specific restrictions imposed by this layer. Refer to FIG. 7 herein. For example, the media layer 10 may be constructed of a uniform material such as for filtering, in configuration but provided with one or more restricting orifices 19 through the surface thereof to control flow rate. The size (diameter) of each orifice 19, as well as the number of orifices determines the flow rate through the tube sheet. Such a media layer thus functions as a throttling mechanism within the tube sheet itself so as to modulate the output flow given some input condition such as flow and/or pressure. A media layer with one or more orifices 19 can also function for filtration through the non-orifice locations. Thus, any one media layer may be considered as having multiple functions. In FIG. 7 the orifices 19 are shown as aligned with the holes 11, however, in other embodiments the orifices may not be so aligned. If the layer 10 is somewhat porous then orifices can be provided at many different locations in layer 10.

Figure 8:
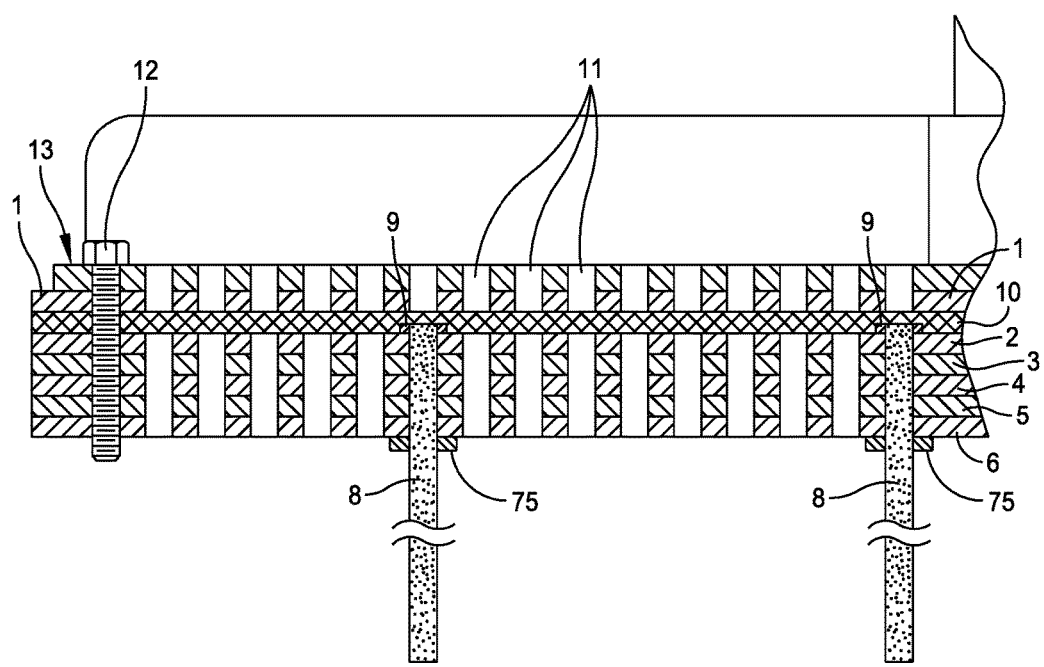
FIG. 8 is a fragmentary cross-sectional view showing another embodiment of the present invention including a securing piece associated with the filter tube.
Figure 9:
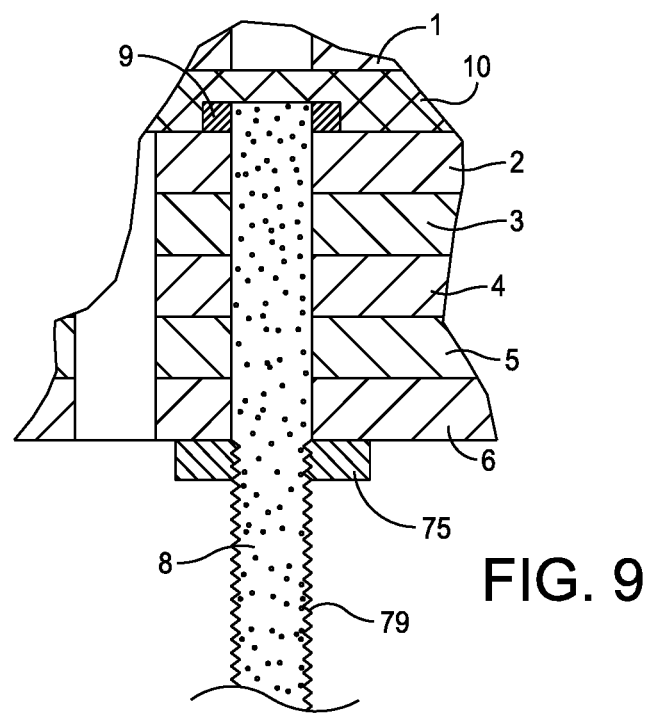
FIG. 9 is an enlarged cross-sectional view showing the construction at one filter tube and employing a securing nut.
Figure 10:
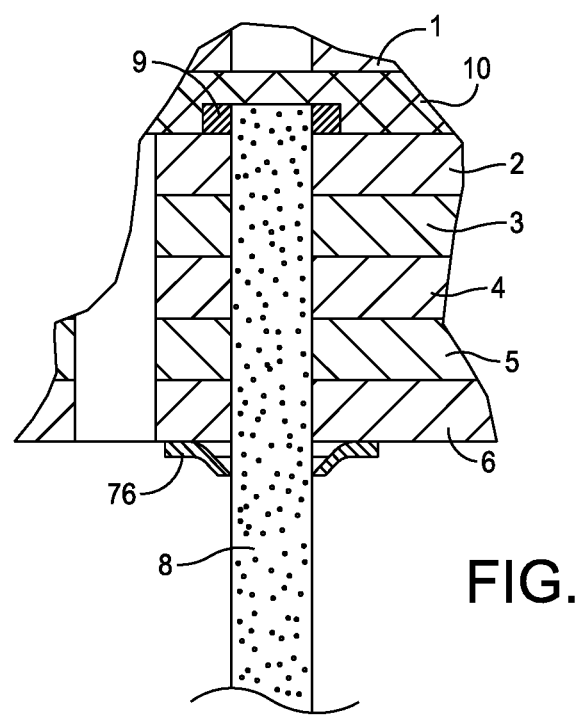
FIG. 10 an enlarged cross-sectional view showing the construction at one filter tube and employing a push nut.
Figure 10A:
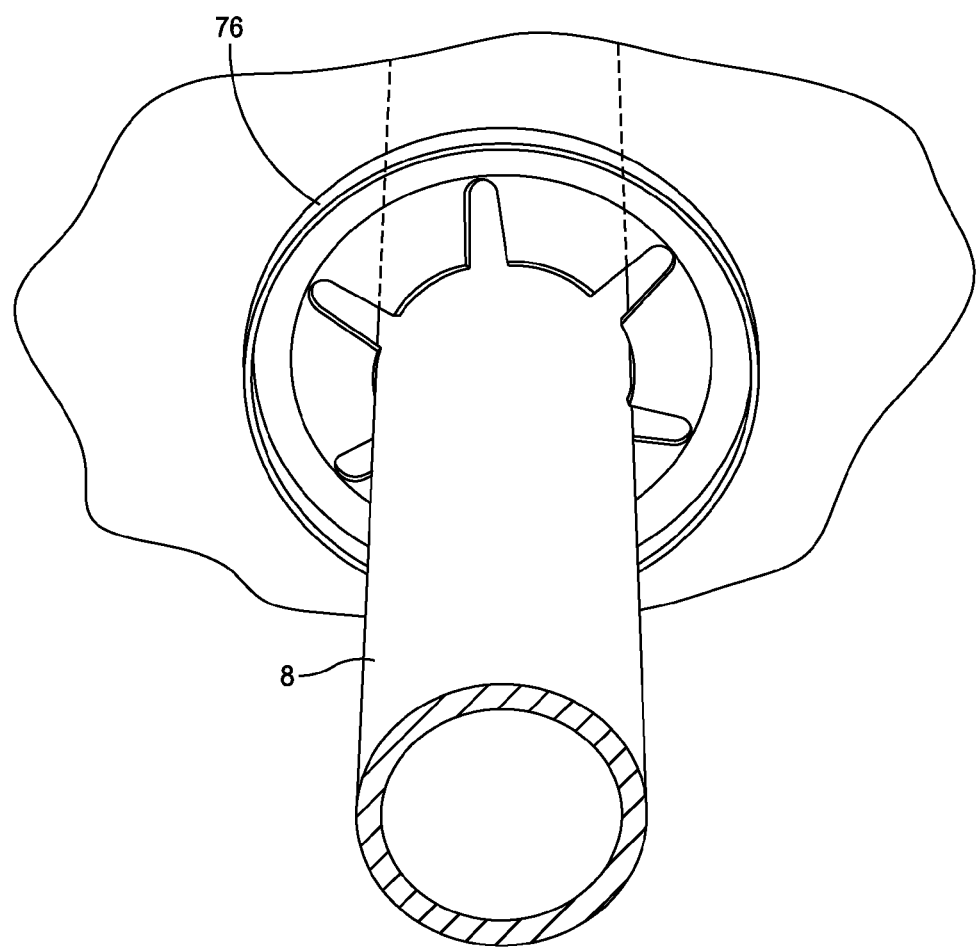
FIG. 10A is a fragmentary perspective view illustrating the push nut disposed on a filter tube
Figure 11:
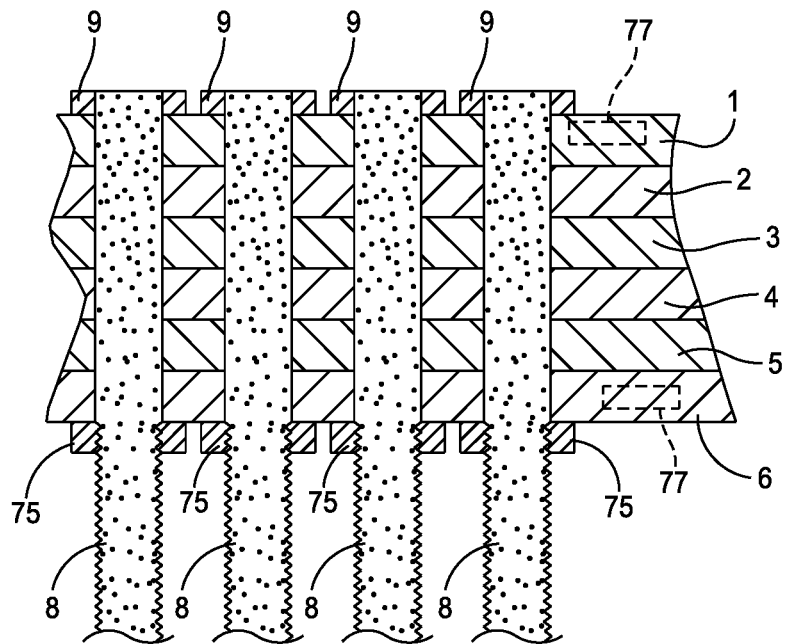
FIG. 11 is a fragmentary cross-sectional view of another embodiment of the present invention employing the securing piece.
Figure 12:
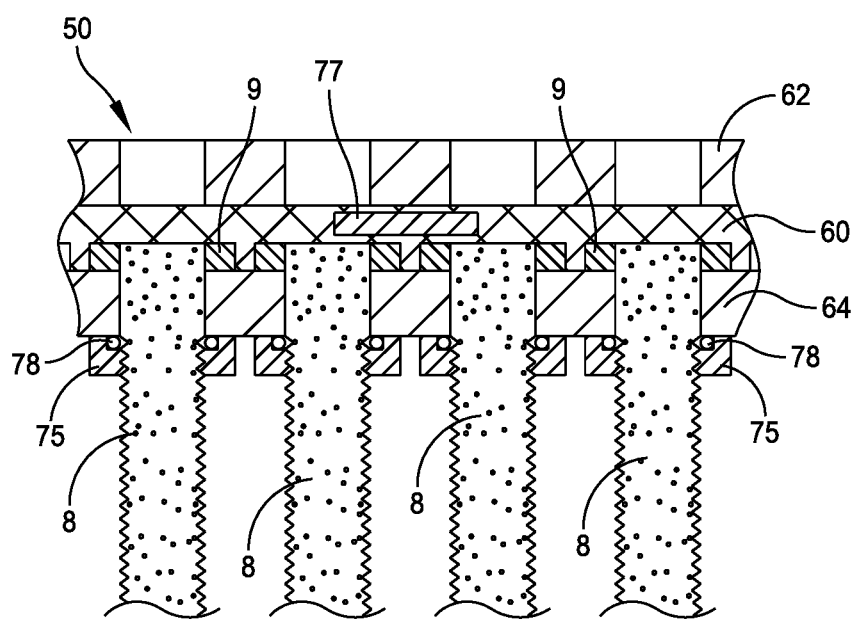
FIG. 12 is a fragmentary cross-sectional view showing the use of the securing piece associated with each filter tube and a sensor.

An alternate embodiment of the present invention is now illustrated in FIGS. 8-12. FIG. 8 is a fragmentary cross-sectional view showing another embodiment of the present invention including a securing piece associated with the filter tube. FIG. 9 is an enlarged cross-sectional view showing the construction at one filter tube and employing a securing nut. FIG. 10 an enlarged cross-sectional view showing the construction at one filter tube and employing a push nut. FIG. 10A is a fragmentary perspective view illustrating the push nut disposed on a filter tube. FIG. 11 is a fragmentary cross-sectional view of another embodiment of the present invention employing the securing piece. FIG. 12 is a fragmentary cross-sectional view showing the use of the securing piece associated with each filter tube and a sensor. The embodiments described in FIGS. 8-12 represent a further improvement to the tube sheet construction. This primarily involves use of a securing piece that is constructed and arranged to be disposed about the tubular element or filter tube and functions, in concert with, the flanged end of the elongated tubular element to provide a compressive force against the tube sheet segments that are disposed between the flanged top end and the securing piece. This construction may be used in a tube sheet construction such as illustrated in the fragmentary cross-sectional view of FIG. 8. In this particular embodiment the tube sheet construction is shown as including a media layer 10, although, the principles of the present invention may also be used in a tube sheet construction where there is no media layer provided.

The fragmentary cross-sectional view of FIG. 8 illustrates the flanged end at 9. This may be constructed of a grommet that is crimped about an end of the elongated hollow tubular element 8. In other embodiments of the present invention, this flanged member 9 may also be crimped about other locations along the elongated tubular element 8. FIG. 8 also illustrates a securing piece in the form of a nut 75 that is threadedly engaged with the element 8. In this regard, refer to the somewhat more detailed fragmentary cross-sectional view of FIG. 9 illustrating the nut at 75 engaged with the elongated tubular shaft 8 which has external threads 79. Reference may also now be made to the fragmentary cross-sectional view of FIG. 10 to show a different embodiment of the securing piece. This is illustrated as in the form of a push nut 76. Refer also to the fragmentary perspective view of FIG. 10A that shows further details of the push nut 76. The push nut 76 functions so that it can be forced onto the shaft of the filter tube but is constructed so that it is locked in place once pushed on and not easily disengaged from the filter tube 8. In FIG. 10 the filter tube 8 is shown as having a smooth outer surface. However in another embodiment of the present invention, it may be provided with small circular indentation rings that assist in the positioning and engagement of the push nut 76 with the filter tube 8.

Reference is now made to FIG. 11 which is a further fragmentary cross-sectional view showing multiple tubular elements 8 with a grommet or flanged end illustrated at 9 and with a securing piece in the form of a nut 75 under the layer 6. The flanged end 9 is disposed above the top layer 1 of the multiple tube sheet segments. The nut 75 is disposed under the bottommost layer 6 of the plurality separate planar tube sheet segments. By tightening the nut 75, there is a compressive force between the nut 75 and the flange 9 providing a compression of the tube sheet segments therebetween. Even though a cover is provided with additional fasteners 12, the tube sheet segments may be relatively large in diameter and by providing the securing pieces as described herein, there is additional compression and additional tension on the tube sheet segments at virtually every location of the filter tubes. Although a securing piece is illustrated at each of the tubes 8 in FIG. 11, it is also possible to provide a securing piece at only predetermined ones of the elongated filter tubes 8. The use of securing pieces can be arranged to provide a series of securing pieces spread throughout the tube sheet construction, each associated with a filter tube as illustrated, so that there are several locations where additional compression is applied. Also, the flanged end 9 is provided so that it engages firmly with a top surface of the engaged tube sheet segment by virtue of the hole in the segment being smaller than the diameter of the flanged end, leaving an annular engagement surface of the flanged end directly against the tube sheet segment surface; usually the upper surface thereof.

One particular advantage of the embodiment illustrated in FIG. 10 with the push nut is that it makes the entire structure more tamper proof or tamper resistant. As also previously indicated, this combination of the flanged end and the securing piece introduces another level of tension for the securing of the tubes to the sheet segments.

Reference is now made to the fragmentary cross-sectional view of FIG. 12 which shows the principles of the flanged end and securing piece applied to a simplified tube sheet construction including layers 60, 62 and 64. In this embodiment there is also provided on each of the filter tubes 8, a flanged end at 9 and a securing piece at 75. In this particular embodiment there may also be provided an O-ring 78 between each of the securing nuts 75 and the layer 74. This O-ring 78 can provide additional sealing between each filter tube and the tube sheet construction. In addition, FIG. 12 also illustrates a sensor 77. Multiples sensors may be provided in the layer 60 although only one sensor 77 is shown in FIG. 12. This may be a temperature or pressure sensor or virtually any other type of sensor such as for flow control. In addition, as illustrated in dotted outline in FIG. 11, sensors 77 may also be provided in different layers of the tube sheet construction. In FIG. 12, the sensor 77 is illustrated in a media layer 60. In FIG. 11 the two sensors 77 shown in dotted outline are in respective planar tube sheet segments 1 and 6. By placing sensors at different locations within the tube sheet construction different parameters can be sensed such as different pressures or temperatures across the tube sheet construction.

Figure 13:
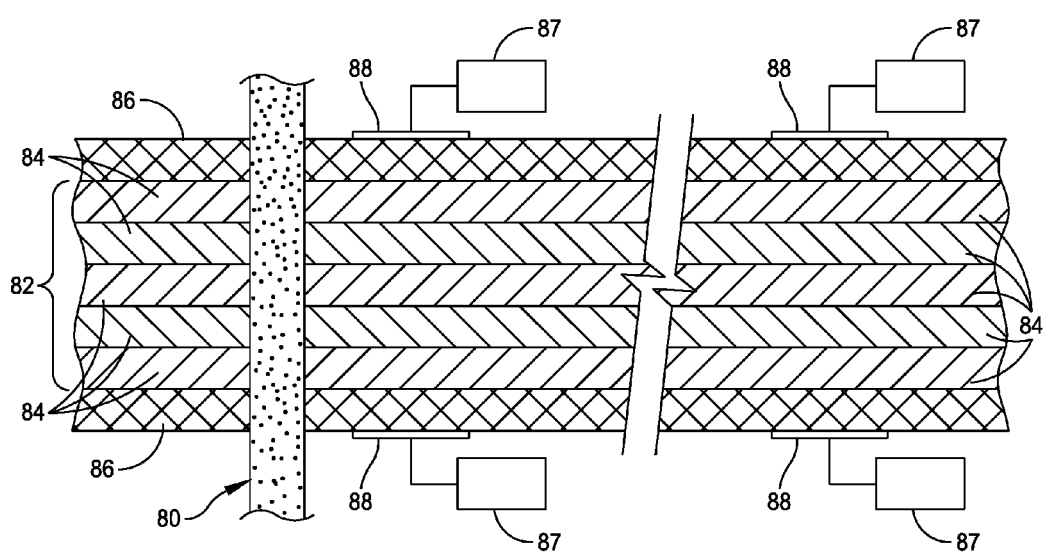
FIG. 13 is a fragmentary cross-sectional view of a portion of a tube sheet construction, related to FIG. 11 but providing further details of the sensors.

Reference is now made to a fragmentary cross-sectional view illustrated in FIG. 13 that provides some additional details for the tube sheet construction. In FIG. 13 only a single tubular element 80 is shown. However, it is understood that as in other embodiments, such as in FIGS. 7, 8, 11 and 12, multiple tubular elements 80 would be employed. Also, although not illustrated in FIG. 13, multiple fasteners would also be provided such as fasteners 12 shown in FIGS. 7 and 8. These fasteners are for securing all of the planar tube sheet segments and the two media layers together and arranged so that all of these various layers are maintained in intimate contact; thus providing a solid tube sheet structure. This media layer in the embodiment of FIG. 13, is identified by the reference character 86. In this embodiment there are two media layers 86 provided disposed parallel with the main tube sheet layers or segments. In FIG. 13 the media layers 86 are disposed one of the top of the tube sheet segments and one at the bottom of the tube sheet segments. These main tube sheet segments are identified by the reference character 82 and are comprised of, in the embodiment of FIG. 13, five separate tube sheet segments 84. Each of the tube sheet segments 84 is planar and the two upper and lower media layers 86 are also planar. Different cross hatching is used in FIG. 13 to depict these layers. The tube sheet layers or segments 84 may be constructed of metal or other tube sheet constructions can be employed as discussed in the various embodiments illustrated herein.

FIG. 13 also illustrates a sensor at 88 associated with each of the media layers 86. Actually, in FIG. 13 there are shown two sensor layers 88 associated with the top media layer 86; and two sensor layers 88 associated with the bottom media layer 86. Each of the sensors 88 are illustrated as coupling to a receiving device 87 which will read a parameter sensed by the sensor 88. The sensors 88 may be sensing any one of a number of different parameters, including, but not limited to, temperature, force and pressure. In essence, the overall tube sheet construction may be considered as a boundary layer of some predetermined dimensions. In the embodiment of FIG. 13, by applying at least one sensor to either or both outer surfaces of layers 86, one is measuring the outer limit of the particular boundary layer.

In FIG. 13 the sensor 88 may be in the form of a printed circuit that can be deposited on an outer surface of either of the media layers 86. In addition, the printed circuit sensor element may be located at other positions of the media layer. For example, FIG. 11 schematically illustrates sensors in dotted outline at 77 and thus, in another embodiment of the present invention, these sensors may be embedded within the respective media layer 86. Also the printed circuit sensor could be deposited on the opposite surface of the media layer 86. For the deposition of a printed circuit layer the media layer itself is preferably electrically non-conductive. In FIG. 13 the opposite side of each media layer 86 would be the side facing one of the tube sheet segments 84. The media layer 86 can be formed of a material that has a certain amount of pliability so that each sensor 88 may be at least partially recessed in its media layer 86 so as to not interfere with a tube sheet segment 84. Also, the cross-sectional area of both the tube sheet segments 84 and the media layers 86 are preferably substantially the same with all fasteners extending through all the tube sheet segments 84 and the media layers 86 to maintain intimate contact between all of the tube sheet segments 84 and the media layers 86.

Having now described a limited number of embodiments of the present invention, it should now be apparent to those skilled in the art that numerous other embodiments and modifications thereof are contemplated as falling within the scope of the present invention, as defined by the appended claims.

What is claimed is:

1. A tube sheet construction comprising a plurality of separate planar tube sheet segments, multiple holes being provided in each planar tube sheet segment in a predetermined pattern, each hole for accommodating an elongated tubular element, wherein all of the tube sheet segments aligned so that each of the predetermined pattern of each tube sheet segment being in alignment, a media layer disposed parallel with the tube sheet segments, at least one sensor element supported by the media layer, and fasteners for securing the planar tube sheet segments and the media layer together and arranged so that all planar tube sheet segments and said media layer are all maintained in intimate contact as a solid tube sheet structure, and wherein each elongated tubular element has a main shaft and an end flange that is integral with the main shaft and that is disposed between the two adjacently disposed tube sheet segments, said end flange having a diameter greater than a diameter of the main shaft of the elongated tubular element.

2. The tube sheet construction of claim 1 wherein the at least one sensor element is imbedded in the media layer.

3. The tube sheet construction of claim 1 including a control monitor external to the tube sheet construction and responsive to a signal from the sensor element, wherein the planar tube sheet segments are each constructed of a metal material and wherein the solid tube sheet structure is without any gaps between adjacent planar metal tube sheet segments and media layer.

4. The tube sheet construction of claim 1 wherein the sensor element senses temperature.

5. The tube sheet construction of claim 1 including multiple sensor elements all supported at the media layer.

6. The tube sheet construction of claim 1 wherein the sensor element senses pressure.

7. The tube sheet construction of claim 1 including a securing piece constructed and arranged about the tubular element, said securing piece for engagement with the tubular shaft to provide a compressive force against the tube sheet segments that are disposed between the flanged top end and the securing piece.

8. The tube sheet construction of claim 1 including a pair of media layers both disposed parallel with all of the tube sheet segments; and at least one sensor element supported at each of both media layers.

9. The tube sheet construction of claim 1 wherein the sensor element comprises a printed circuit sensor and further including a detection device coupled to the printed circuit sensor.

10. The tube sheet construction of claim 1 including at least one of a stimulus device coupled to the media layer for stimulating the media layer and a sensing device coupled to the media layer for sensing a parameter at the media layer.

11. The tube sheet construction of claim 1 wherein the media layer is an active layer, in combination with a stimulus device for applying a stimulus to the active layer.

12. The tube sheet construction of claim 11 wherein the stimulus device is for applying a magnetic field to the active layer.

13. The tube sheet construction of claim 1 wherein the media layer is an active layer, in combination with a stimulus device for applying a stimulus to the active layer, and wherein the stimulus device is comprised of one of an electrical charging circuit, a battery device, and a magnetic flux device.

14. A tube sheet construction that is comprised of a plurality of separate planar tube sheet segments, multiple holes being provided in each planar tube sheet segment in a predetermined pattern, each hole for accommodating an elongated tubular element, all of the tube sheet segments being aligning so that the hole pattern of each segment aligns with the hole pattern in all other segments, a media layer disposed parallel with the tube sheet segments, at least one sensor element supported by the media layer, and fasteners for securing all of the planar tube sheet segments and the media layer together and arranged so that all planar tube sheet segments and said media layer are all maintained in intimate contact so as to form a solid tube sheet structure, and wherein the planar tube sheet segments are constructed of a non-magnetic material and the media layer is constructed of a magnetic material.

15. The tube sheet construction of claim 14 wherein the planar tube sheet segments are constructed of a material that exhibits magnetic susceptibility.

16. A heat exchanger apparatus that includes a tube sheet construction that is comprised of a shell having inlet and outlet plenums and fluid inlet and outlet ports, and a tube sheet construction disposed in the shell, the tube sheet construction including at least two separate tube sheets and a plurality of tubes that extend between the separate tube sheets, wherein each tube sheet includes at least two planar tube sheet segments and a media layer disposed parallel with the tube sheet segments, and at least one sensor element supported by each of the media layers, and fasteners for securing the planar tube sheet segments and the media layer together and arranged so that the planar tube sheet segments and said media layer are all maintained in intimate contact so as to form each of the tube sheets, including multiple holes being provided in each tube sheet in a predetermined pattern, each hole for accommodating a tube sheet tube, the tube sheet segments being aligning so that the hole patterns of each of the tube sheets align, wherein the planar tube sheet segments are each constructed of a metal material and wherein the tube sheet structure is without any gaps between the planar metal tube sheet segments and media layer.

17. The tube sheet construction of claim 16 wherein the at least one sensor element is imbedded in the media layer.

18. The tube sheet construction of claim 16 including a control monitor external to the tube sheet construction and responsive to a signal from each sensor element.

19. The tube sheet construction of claim 18 wherein the sensor element senses temperature.

20. The tube sheet construction of claim 16 including a pair of media layers with a first media layer and a second media layer, the first media layer disposed on one side of one of the tube sheet segments and a second media layer disposed on the opposed side the one of the tube sheet segments.

21. The tube sheet construction of claim 20 including a sensor element supported at each of the media layers.

22. The tube sheet construction of claim 21 wherein each sensor element comprises a printed circuit element coupled to a sensing device.

* * * * *